(12) United States Patent
Drenzek (10) Patent No.: US 11,435,299 B2
(45) Date of Patent: Sep. 6, 2022

(54) CORE ANALYSIS SYSTEM AND RELATED METHODS

(71) Applicant: Baker Hughes Oilfield Operations LLC, Houston, TX (US)

(72) Inventor: Nicholas Drenzek, Oklahoma City, OK (US)

(73) Assignee: Baker Hughes Oilfield Operations LLC, Houston, TX (US)

( * ) Notice: Subject to any disclaimer, the term of this patent is extended or adjusted under 35 U.S.C. 154(b) by 218 days.

(21) Appl. No.: 16/556,880

(22) Filed: Aug. 30, 2019

(65) Prior Publication Data

US 2021/0063325 A1    Mar. 4, 2021

(51) Int. Cl.
*G06K 9/00* (2022.01)
*G01N 23/046* (2018.01)
(Continued)

(52) U.S. Cl.
CPC ......... *G01N 23/046* (2013.01); *G06T 7/0004* (2013.01); *G06T 11/008* (2013.01); *G01N 2223/419* (2013.01); *G01N 2223/616* (2013.01); *G06T 2207/10081* (2013.01); *G06T 2207/30181* (2013.01)

(58) Field of Classification Search
CPC ............. G01N 33/24; G01N 2291/011; G01N 2291/0232; G01N 2291/0289; G01N 2291/105; G01N 29/07; G01N 29/223; G01N 29/227; G01N 3/00; G01N 24/081; G01N 15/0227; G01N 15/1459; G01N 15/1463; G01N 2015/1486; G01N 2015/1497; G01N 33/2823; G01N 15/088
See application file for complete search history.

(56) References Cited

U.S. PATENT DOCUMENTS

| 4,782,501 A | 11/1988 | Dixon, Jr. |
| 5,493,226 A | 2/1996 | Honarpour et al. |

(Continued)

FOREIGN PATENT DOCUMENTS

CN    107036911 A    8/2017

OTHER PUBLICATIONS

International Search Report for International Application No. PCT/US2020/047658, dated Dec. 4, 2020, 3 pages.

(Continued)

*Primary Examiner* — Alex Kok S Liew
(74) *Attorney, Agent, or Firm* — TraskBritt (57) ABSTRACT

Embodiments include systems and methods for determining properties of a formation including disposing a core sample of the formation within a core holder assembly, applying pressures to the core sample, rotating the core sample about a center longitudinal axis of the core holder assembly, obtaining a series of computed tomography images of the core sample at different rotation increments of the core sample, generating, based at least partially on the obtained series of computed tomography images of the core sample, a 3D representation of the core sample utilizing a radon transform, measuring a displacement of at least one characteristic of the core sample due to the applied pressures, and based at least partially on the measured displacement, determining at least one property of the formation as a function of the applied pressures.

20 Claims, 6 Drawing Sheets

(51) Int. Cl.
*G06T 7/00* (2017.01)
*G06T 11/00* (2006.01)

(56) References Cited

U.S. PATENT DOCUMENTS

| | | |
|---|---|---|
| 8,356,510 B2 | 1/2013 | Coenen |
| 9,903,826 B2 | 2/2018 | Alshehri et al. |
| 10,139,355 B1 | 11/2018 | Li et al. |
| 2003/0084715 A1* | 5/2003 | Zazovsky ............. E21B 49/005 73/152.05 |
| 2003/0142778 A1* | 7/2003 | Proksa ................... A61B 6/027 378/4 |
| 2012/0243656 A1 | 9/2012 | Jin et al. |
| 2017/0275970 A1* | 9/2017 | Crawford ............. G01V 99/005 |

OTHER PUBLICATIONS

International Written Opinion for International Application No. PCT/US2020/047658, dated Dec. 4, 2020, 6 pages.

\* cited by examiner

CORE ANALYSIS SYSTEM AND RELATED METHODS

TECHNICAL FIELD

Embodiments of the present disclosure relate generally to methods and apparatuses for determining properties of formations via analysis of core samples.

BACKGROUND

Oil wells (wellbores) are usually drilled with a drill string. The drill string includes a tubular member having a drilling assembly that includes a single drill bit at its bottom end. The drilling assembly may also include devices and sensors that provide information relating to a variety of parameters relating to the drilling operations ("drilling parameters"), behavior of the drilling assembly ("drilling assembly parameters") and parameters relating to the formations penetrated by the wellbore ("formation parameters"). A drill bit and\or reamer attached to the bottom end of the drilling assembly is rotated by rotating the drill string from the drilling rig and/or by a drilling motor (also referred to as a "mud motor") in the bottom hole assembly ("BHA") to remove formation material to drill the wellbore.

Rock mechanical properties (e.g., stress-strain curves and compressive and shear strengths) of a formation are key inputs to hydraulic fracturing and completion models. As such, certain lithological properties of the formation and/or a subterranean reservoir are usually determined. Conventionally, the rock mechanical properties can be determined and/or estimated via downhole sonic logs or via lab load frames equipped with axial and radial displacement sensors. However, the foregoing methods do not provide mechanical properties at the grain scale that affect far-field (wellbore distal) fracture propagation in unconventional reservoirs, which can lead to errors in fracture models and attendant completion designs. Additionally, changes in rock mechanical properties with mineralogy, which is an input for "brittleness" and/or "fraccability" logs cannot be determined at these scales using the foregoing methods. Furthermore, sonic logs are typically relatively expensive and can be subject to calibration/interpretation error, and load frame measurements are time-sensitive, relatively expensive, and can be subject to other experimental difficulties (e.g., health, safety, and environmental limitations, as well as high temperature limitations).

BRIEF SUMMARY

Some embodiments of the present disclosure include a method of determining properties of a core sample. The method may include disposing a core sample of a formation within a core holder assembly, applying one or more pressures to the core sample; obtaining at least one computed tomography image of the core sample, and based on the at least one computed tomography image of the core sample, determining at least one property of the core sample as a function of the applied one or more pressures.

Further embodiments of the present disclosure include a core analysis system for determining properties of a core sample. The core analysis system may include a core holder assembly, a computed tomography imager; and a core-analysis control system operably coupled to the core holder assembly and the computed tomography imager. The core-analysis control system may include: at least one processor and at least one non-transitory computer-readable storage medium storing instructions thereon that, when executed by the at least one processor, cause the core analysis system to: apply, via the core holder assembly, one or more pressures to a core sample of a formation disposed within the core holder assembly, rotate the core holder assembly about a center longitudinal axis of the core holder assembly, obtain, via the computed tomography imager, a series of computed tomography images of the core sample at different rotation increments of the core holder assembly, generate, based on the series of computed tomography images of the core sample, a three-dimensional representation of at least a portion the core sample utilizing a radon transform, and measure a displacement of at least one characteristic of the core sample due to the applied pressures.

Some embodiments of the present disclosure include a method of determining properties of a core sample. The method may include disposing a core sample of a formation within a core holder assembly, applying one or more pressures to the core sample; rotating the core sample about a center longitudinal axis of the core holder assembly, obtaining a series of computed tomography images of the core sample at different rotation increments of the core sample, generating, based at least partially on the obtained series of computed tomography images of the core sample, a three-dimensional representation of at least a portion of the core sample utilizing a radon transform, measuring a displacement of at least one characteristic of the core sample due to the applied one or more pressures, and based at least partially on the measured displacement, determining at least one property of the core sample as a function of the applied one or more pressures.

DETAILED DESCRIPTION

In the following description, reference is made to the accompanying drawings in which is shown, by way of illustration, specific embodiments of the present disclosure. The embodiments are intended to describe aspects of the disclosure in sufficient detail to enable those skilled in the art to practice the invention. Other embodiments may be utilized and changes may be made without departing from the scope of the disclosure. The following detailed description is not to be taken in a limiting sense, and the scope of the present invention is defined only by the appended claims.

As used herein, the singular forms following "a," "an," and "the" are intended to include the plural forms as well, unless the context clearly indicates otherwise.

As used herein, the term "may" with respect to a material, structure, feature, or method act indicates that such is contemplated for use in implementation of an embodiment of the disclosure, and such term is used in preference to the more restrictive term "is" so as to avoid any implication that other compatible materials, structures, features, and methods usable in combination therewith should or must be excluded.

As used herein, any relational term, such as "first," "second," "top," "bottom," "upper," "lower," etc., is used for clarity and convenience in understanding the disclosure and accompanying drawings, and does not connote or depend on any specific preference or order, except where the context clearly indicates otherwise. For example, these terms may refer to an orientation of elements of a core analysis system in an operating orientation. Furthermore, these terms may refer to an orientation of elements of a core analysis system when as illustrated in the drawings.

As used herein, the term "substantially" in reference to a given parameter, property, or condition means and includes to a degree that one skilled in the art would understand that the given parameter, property, or condition is met with a small degree of variance, such as within acceptable manufacturing tolerances. By way of example, depending on the particular parameter, property, or condition that is substantially met, the parameter, property, or condition may be at least 90.0% met, at least 95.0% met, at least 99.0% met, or even at least 99.9% met.

As used herein, the term "about" used in reference to a given parameter is inclusive of the stated value and has the meaning dictated by the context (e.g., it includes the degree of error associated with measurement of the given parameter, as well as variations resulting from manufacturing tolerances, etc.).

Some embodiments of the present disclosure include methods for generating three-dimensional representations (e.g., a volumetric maps of X-ray attenuation) of a core sample of a formation to determine/calculate grain-scale and/or sample size-scale displacement as a function of applied axial and/or radial loads (e.g., pressures, stresses, forces, etc.) and/or pore fluid loads (e.g., pressure, stresses, forces, etc.). Determining the grain-scale and/or sample size-scale displacement(s) as a function of applied axial and/or radial loads and/or pore fluid loads leads to determining rock mechanical properties at the grain-scale and/or sample size-scale and between the foregoing scales. The method includes scanning a high-pressure rated, minimally X-ray attenuating, core holder assembly (e.g., a Hassler-type core holder) with a CT scanner and acquiring one or more projection images (CT images) as a function of applied stress (e.g., an applied load profile, an applied pressure profile, an applied stress profile, an applied force profile, etc.).

Figure 1A:
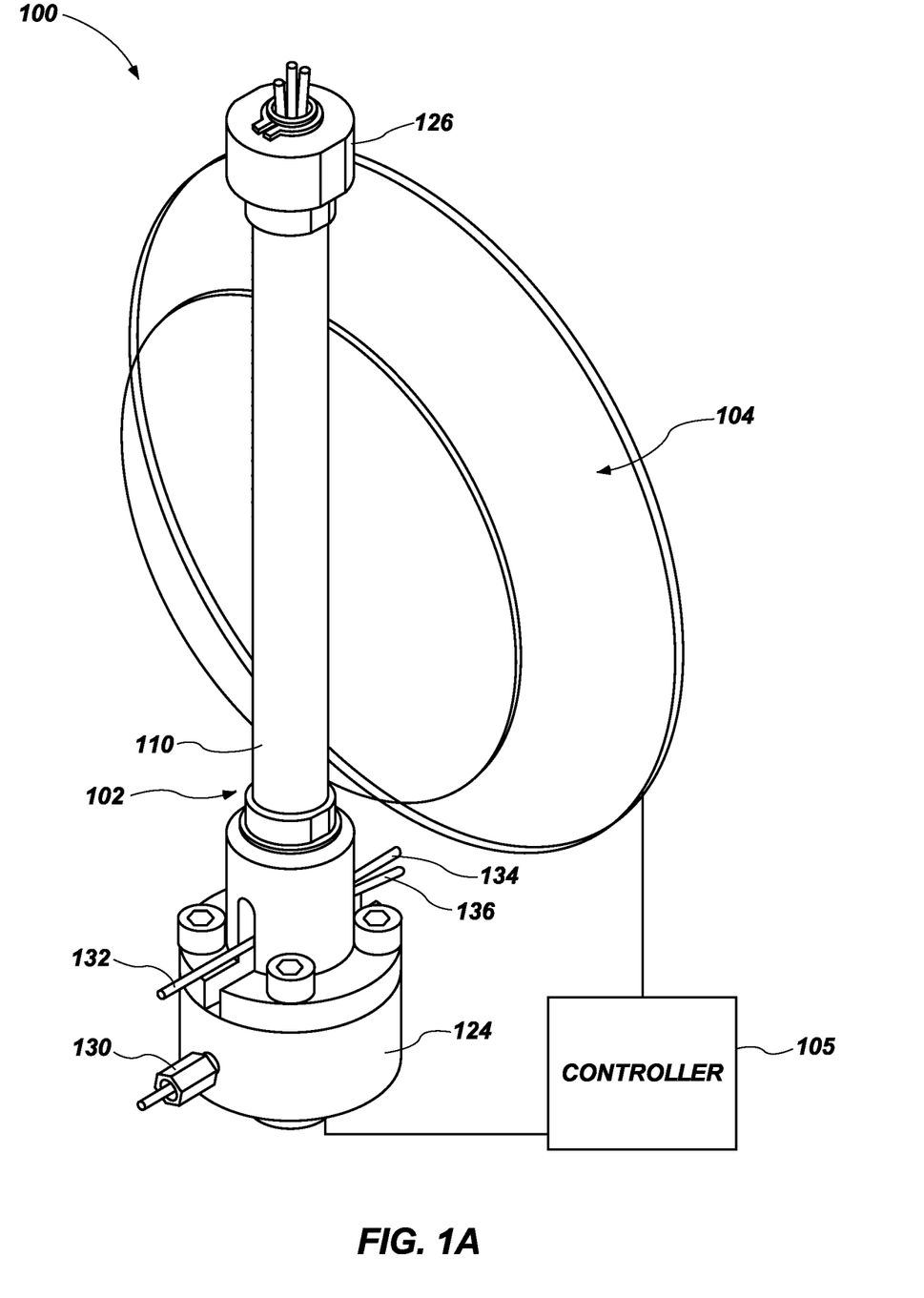
FIGS. 1A-1D show various views of a core holder assembly according to one or more embodiments of the present disclosure.
Figure 1B:
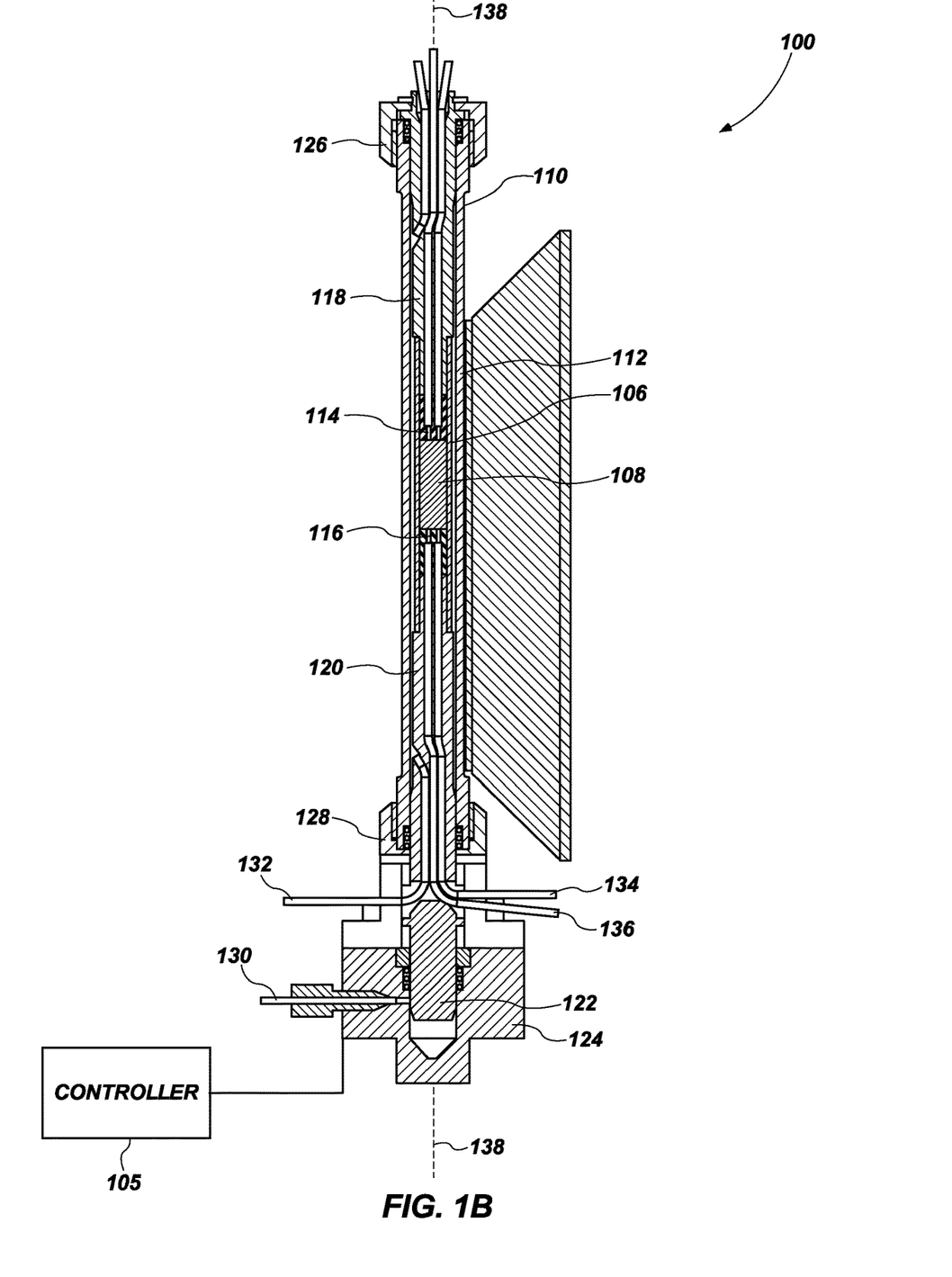
Figure 1C:
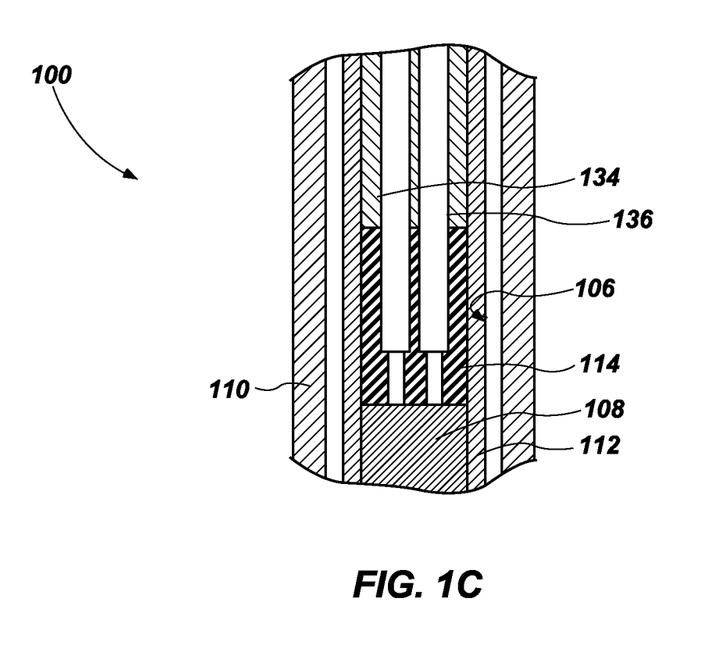
Figure 1D:
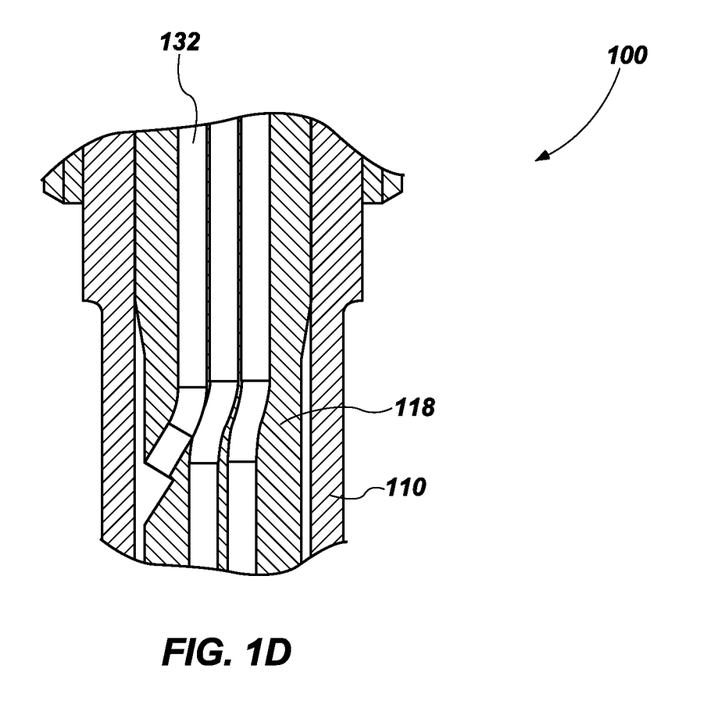

FIG. 1A shows perspective view of a core analysis system 100 according to one or more embodiments of the present disclosure. FIG. 1B shows a side cross-sectional view of the core analysis system 100 of FIG. 1A. FIGS. 1C and 1D show enlarged partial cross-sectional views of the core analysis system 100 of FIGS. 1A and 1B. Referring to FIGS. 1A-1D together, the core analysis system 100 may include a core holder assembly 102, an imager system 104, and controller 105.

In some embodiments, the core holder assembly 102 may be similar to conventional Hassler-type core holders. In particular, the core holder assembly 102 may define a holding chamber 106 (e.g., a pressure chamber) for holding and applying loads (e.g., pressures) to a core sample 108. In one or more embodiments, the core holder assembly 102 may include a tubular body 110, a core sample sleeve 112, a first end plug 114, a second end plug 116, a first core piston 118, a second core piston 120, a hydraulic piston 122, a hydraulic piston housing 124, a first end cap 126, a second end cap 128, a hydraulic fluid input 130, a confining fluid line 132, a first flooding fluid line 134, and a second flooding fluid line 136.

The tubular body 110 may define an outer body of the core holder assembly 102, and the tubular body 110 may define a cylindrical hole extending therethrough. The core sample sleeve 112 may be sized and shaped to receive the core sample 108 of a formation. The first and second end plugs 114, 116 may be disposed on opposite ends of the core sample 108, and the first and second end plugs 114, 116 may be disposed at least partially within the core sample sleeve 112. The first and second core pistons 118, 120 may be disposed on opposite ends of the core sample 108 and may be in contact with the first and second end plugs 114, 116, respectively. The hydraulic piston housing 124 may be coupled to a longitudinal end (e.g., a lower longitudinal end) of the tubular body 110 and may house the hydraulic piston 122. The hydraulic piston 122 may be operably coupled to the second core piston 120, such that movement of the hydraulic piston 122 along a center longitudinal axis 138 of the core holder assembly 102 causes movement of the second core piston 120.

The first end cap 126 may be disposed on a longitudinal end of the tubular body 110 opposite the hydraulic piston housing 124, and the second end cap 128 may be disposed at an interface of the tubular body 110 and the hydraulic piston housing 124. The hydraulic fluid input 130 may extend into the hydraulic piston housing 124 and may interact with the hydraulic piston 122 in a conventional manner to cause the hydraulic piston 122 to move within the hydraulic piston housing 124. The confining fluid line 132 may extend to an annular space around the core sample sleeve 112 such that fluid input into the confining fluid line 132 can apply a confining load (e.g., a radial load, a radial pressure, etc.) to the core sample 108. Furthermore, the first flooding fluid line 134 and the second flooding fluid line 136 may extend to the second end plug 116 and may extend from the second end plug 116 such that a flooding fluid can be passed through the core sample 108.

In one or more embodiments, the core holder assembly 102 may further include a porous disc disposed adjacent to each longitudinal end of the core sample 108. The porous discs may enable the flooding fluid to interact with (e.g., flood) the core sample 108.

In some embodiments, the core sample sleeve 112 may include a flexible material to enable a confining load to be applied to the core sample 108 while protecting the core sample 108 from the confining fluid. For example, the core sample sleeve 112 may include a rubber material or a flexible polymer. As a non-limiting example, the core sample sleeve 112 may include Viton 70 rubber.

In view of the foregoing, the core holder assembly 102 may operate in substantially the same manner as a conventional Hassler-type core holder. For instance, the first and second pistons 118, 120, via the hydraulic piston 122 and a hydraulic fluid (e.g., hydraulic oil), may be utilized to apply an axial load (e.g., an axial pressure) to the core sample 108 in conventional manners, and the confining fluid line 132 and a confining fluid (e.g., a hydraulic fluid) may be utilized to apply a confining load (e.g., a radial load) to the core sample 108. Furthermore, the first and second flooding lines 134, 136 and one or more flooding fluids (e.g., brine and oil) can be utilized to apply pore fluid pressures within a pore network of the core sample 108. In view of the foregoing, the core holder assembly 102 may simulate in-situ stresses within the core sample 108 and may be utilized to incrementally apply axial loads, radial loads, and/or pore fluid pressures.

In one or more embodiments, the materials of the core holder assembly 102 or at least the materials around the core sample 108 within the core holder assembly 102 may be at least substantially x-ray transparent materials. For instance, one or more of the tubular body 110, the core sample sleeve 112, the first end plug 114, the second end plug 116, the first core piston 118, the second core piston 120, the hydraulic piston 122, the hydraulic piston housing 124, the first end cap 126, the second end cap 128, the hydraulic fluid input 130, the confining fluid line 132, the first flooding fluid line 134, and the second flooding fluid line 136 may comprise radiolucent structural materials. Furthermore, the radiolucent structural materials may include AlbeMet™ (a beryllium and aluminum matrix composite), PEEK (polyetheretherketone), Viton 70, carbon-fiber plastic composites, thermoplastics (e.g., nylons, polycarbonates, and polyketones), materials having a low-effective-atomic number, and/or low-electron-density materials. Additionally, in some embodiments, one or more of the first core piston 118, the second core piston 120, the confining fluid line 132, the first flooding fluid line 134, or the second flooding fluid line 136 may include Hastelloy™ C (a nickel-chromium-molybdenum-tungsten alloy), and one or more of the first and second end caps may include AM7 AluBronze.

Figure 2:
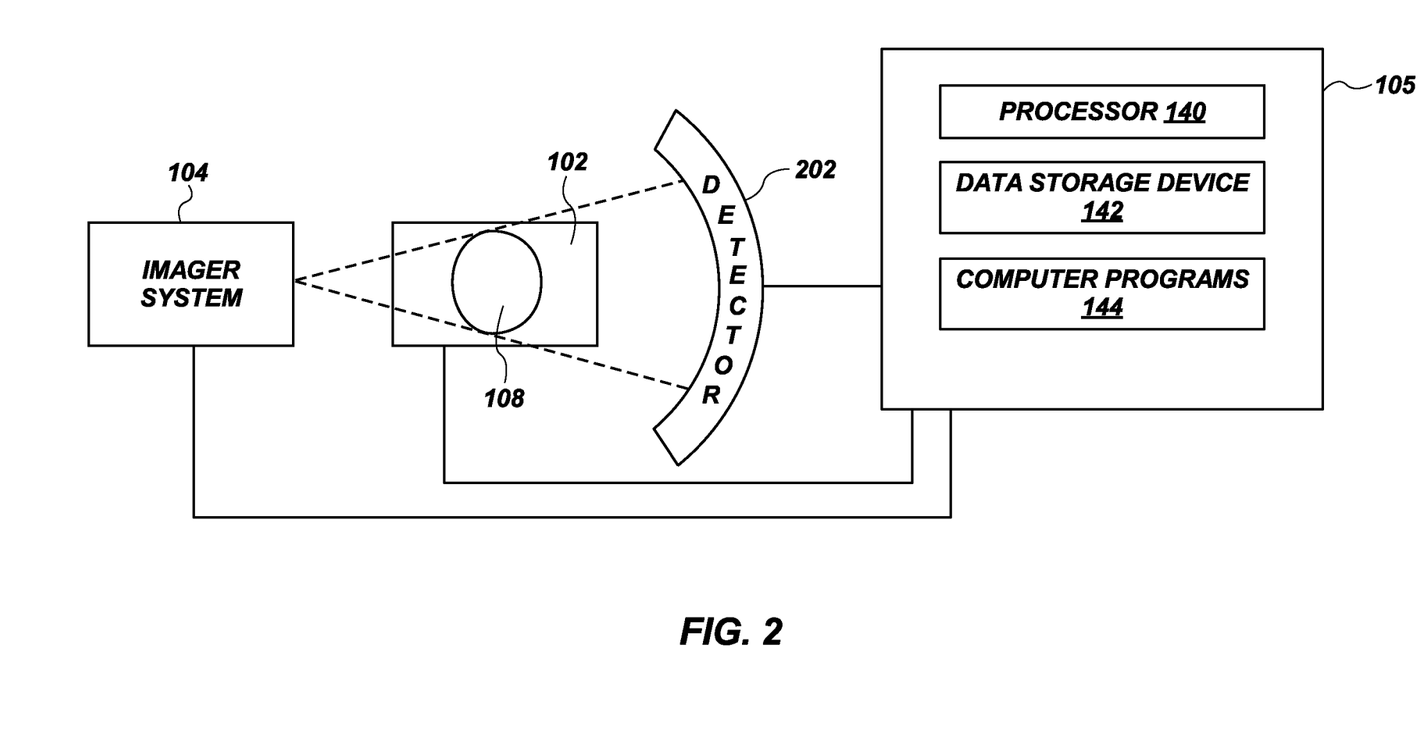
FIG. 2 shows a schematic view of a core analysis system according to one or more embodiments of the present disclosure.

As noted above, the core analysis system 100 may further include the imager system 104 and the controller 105. FIG. 2 is a schematic representation of the core analysis system 100 according to one or more embodiments of the present disclosure. Referring to FIGS. 1A-2 together, in one or more embodiments, the imager system 104 may include a computed tomography (CT) scanner or micro-CT scanner. For instance, the imager system 104 may generate X-rays (e.g., X-ray energy) that are passed through the core holder assembly 102 and the core sample 108 and collected by a detector 202 to acquire images of the core sample 108 along an axis of the core sample 108 (e.g., a two-dimensional slice of the core sample 108). Furthermore, the detector 202 outputs collected X-ray data to a data processing unit of the controller 105. As a non-limiting example, the imager system 104 may include any conventional CT scanner or micro-CT scanner known in the art and any conventional collector (detector 202) known in the art. In further embodiments, the imager system 104 may include a magnetic resonance imaging (MRI) system in conjunction with an MRI amenable stress cell.

The controller 105 may be operably coupled to the core holder assembly 102 and the imager system 104 and may be configured to control the operations of the core holder assembly 102 and the imager system 104. The controller 105 may include a processor 140 and a data storage device 142 (or a computer-readable medium) for storing data, algorithms, and computer programs 144. The data storage device 142 may be any suitable device, including, but not limited to, a read-only memory (ROM), a random-access memory (RAM), a flash memory, a magnetic tape, a hard disk, and an optical disc. Additionally, the controller 105 may further include one or more devices for presenting output to an operator of the core analysis system 100, including, but not limited to, a graphics engine, a display (e.g., a display screen), one or more output drivers (e.g., display drivers), one or more audio speakers, and one or more audio drivers. In certain embodiments, the controller 105 is configured to provide graphical data to a display for presentation to an operator. The graphical data may be representative of one or more graphical user interfaces and/or any other graphical content as may serve a particular implementation.

As is described in greater detail herein, the controller 105 may cause the core holder assembly 102 to apply loads to a core sample 108 and to rotate relative to the imager system 104, and the controller 105 may cause the imager system 104 to capture (e.g., obtain) one or more series of image (e.g., CT scans) of the core sample 108. Additionally, the controller 105 may cause the core analysis system 100 (e.g., the combination of the processor 140, the data storage device 142, and the computer programs 144) to measure displacements of characteristics of the core sample 108 in one or more dimensions (e.g., dimensions orthogonal to a given image of the series of images) that are caused by the applied loads. As used herein, the term "characteristics" may include pore boundaries, pore volumes, grain boundaries, grain volumes, electron densities, photoelectric effects, fractures or cracks, and/or outer surfaces of the core sample 108. Based at least partially on the measured displacements, the controller 105 may further cause the core analysis system 100 to determine one or more properties (e.g., rock mechanical properties) of a formation from which the core sample 108 is taken. As used herein, the term "properties" and its derivatives, when used in reference to a formation or a core sample, includes confined compressive strength, unconfined compressive strength, Poisson's ratio in multiple directions, a porosity (e.g., a derived porosity), a permeability (e.g., a simulated permeability), a bulk density, a grain density, a bulk-grain density porosity, a chemical and/or mineral property including mineralogy, grain/clast size, a flexural moduli, a composition, and/or an effective failure stress.

Furthermore, in some embodiments, the controller 105 may be local to the remainder of the core analysis system 100. In other embodiments, the controller 105 may be remote to remainder of the core analysis system 100. The controller 105 is described in greater detail below with reference to FIG. 4.

Figure 3:
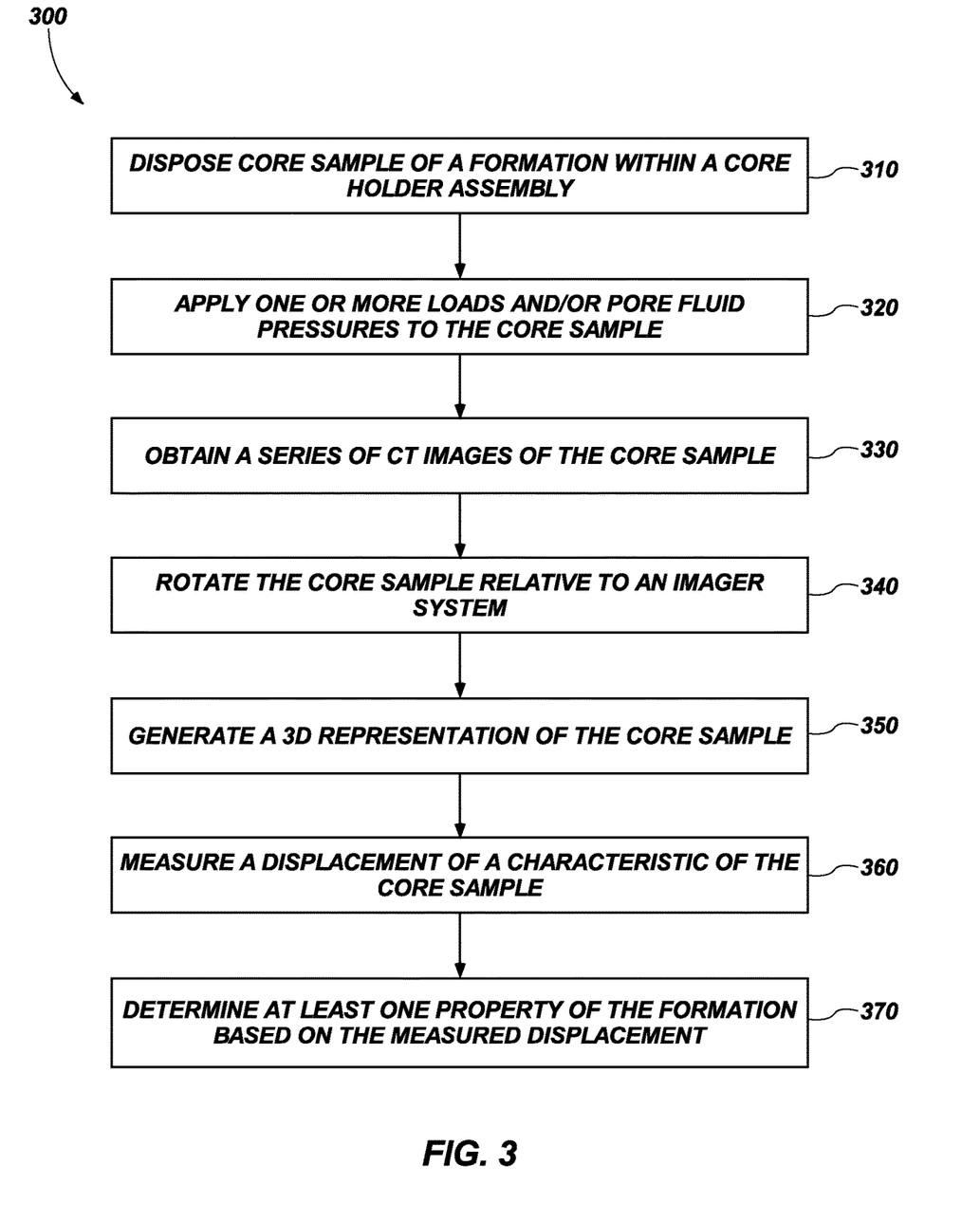
FIG. 3 shows a flow chart of a method of determining a property of a formation according to one or more embodiments of the present disclosure.

FIG. 3 is an example flow chart of a method 300 of determining one or more properties of a formation and/or core sample (e.g., core sample 108). In one or more embodiments, the method 300 may include disposing a core sample 108 of a formation within a core holder assembly 102 of a core analysis system 100, as shown in act 310. For instance, the method 300 may include disposing the core sample 108 within a core sample sleeve 112 and between a first end plug 114 and a second end plug 116 in conventional manners. Furthermore, the method 300 may include disposing the core sample 108 within a tubular body 110 of the core holder assembly 102.

In one or more embodiments, the core sample 108 may have dimensions in any given axis of less than 100 mm. For instance, in some embodiments, the core sample 108 may have a diameter of less than 10 mm, and a length of less than 50 mm.

The method 300 may further include applying one or more loads and/or pore fluid pressures to the core sample 108 within the core holder assembly, as shown in act 320. In some embodiments, the one or more loads may include axial loads (e.g., axial pressures) and radial loads (e.g., confining loads, confining pressures, etc.). In such embodiments, the method 300 may include applying the axial loads by, for example, compressing the core sample 108 via a first core piston 118, a second core piston 120, and a hydraulic piston 122 via conventional manners utilized with Hassler-type core holders. For example, a hydraulic fluid may be inserted and/or extracted from a hydraulic piston housing 124 to cause the hydraulic piston 122 to translate within the hydraulic piston housing, and as a result, cause the second core piston 120 to apply loads to the core sample 108.

The radial loads may be applied via a confining fluid and a confining fluid line 132. For instance, as noted above in regard to FIGS. 1A-1D, a confining fluid may be inserted into an annular space around the core sample sleeve 112, which is made of a flexible material, and the confining fluid may be pressurized. As a result, the confining fluid may exert forces on the core sample 108 in a radial direction (e.g., in a direction toward a center longitudinal axis of the core sample 108). In other words, the confining fluid may subject the core sample 108 to pressures in conventional manners.

Furthermore, as noted above, in some embodiments, the method 300 may include applying one or more pore fluid pressures to the core sample 108. For instance, via a first flooding fluid line 134 and a second flooding fluid line 136, the core sample 108 may be flooded (e.g., saturated) with or at least partially exposed to a flooding fluid. In some embodiments, the flooding fluid may be pressurized to subject the core sample 108 to a pore fluid pressure. In additional embodiments, the core sample 108 may be saturated with the flooding fluid and subjecting the core sample 108 to the other loads described above may cause the core sample 108 to compress, which may cause the core sample 108 to experience pore fluid pressures due to the presence of the flooding fluid. As will be understood by one of ordinary skill in the art, any of the above-described loads and pore fluid pressures may be applied in combination with each other.

In one or more embodiments, the method 300 may include applying the one or more loads and/or pore fluid pressures to simulate in-situ stresses that a formation may experience during a conventional drilling operation. Additionally, as is described in greater detail below, the method 300 may include applying the one or more loads and/or pore fluid pressures incrementally and/or simultaneously with any of the below-described acts of the method 300. Furthermore, in some embodiments, the method 300 may include applying the loads until effective failure (e.g., structural failure) of the core sample 108 or until a specific displacement and/or deformation is achieved.

The method 300 may also include obtaining (e.g., capturing) a series of CT images of the core sample 108, as shown in act 330 of FIG. 3. For instance, the method 300 may include causing the imager system 104 to capturing an image (e.g., a micro-CT image) of the core sample 108 along one axis (e.g., one plane). Furthermore, the method 300 may include rotating the core sample 108 relative to the imager system 104, as shown in act 340 of FIG. 3 and described in greater detail below. In view of the foregoing, the method 300 may include capturing the series of CT images of the core sample 108 while rotating the core sample 108. As a non-limiting example, the method 300 may include capturing a first image of the series of CT images, then rotating the core sample a certain amount of rotation, and capturing a second image of the series of CT images. In some embodiments, the foregoing procedure can be repeated until the core sample 108 have been rotated by 360°. In one or more embodiments, a CT image may be acquired at every degree of rotation. In additional embodiments, a CT image may be acquired at every half-degree of rotation. In further embodiments, a CT image may be acquired at every fourth of a degree of rotation. Although specific amounts of rotation are described herein, one of ordinary skill in the art will readily recognize that a CT image may be acquired after any amount of rotation of the core sample 108.

In some embodiments, the method 300 may include applying a constant (e.g., a same) load through the entire 360° of rotation. For example, any applied loads and/or pore fluid pressures may be constant through the full rotation. In other embodiments, any applied loads and/or pore fluid pressures may be changed at one or more points throughout the rotation. For example, the applied loads and/or pore fluid pressures may be incrementally changed throughout the rotation.

In one or more embodiments, the method 300 may include obtaining (e.g., capturing) multiple series of CT images of the core sample 108. For instance, a first series of CT images of the core sample 108 may be acquired via any of the manner described above and at a first constant set of applied loads and/or pore fluid pressures (i.e., referred to herein also as a "load profile"), and a second series of CT images of the core sample 108 may be acquired via any of the manner described above and at a second constant set of applied loads and/or pore fluid pressures (e.g., an incrementally changed set of applied loads and/or pore fluid pressures) (e.g., a second load profile). For example, one or more of the applied loads and/or pore fluid pressures may be incrementally changed in the second constant set relative to the first constant set. Furthermore, the method 300 may include obtaining a third, fourth, fifth, sixth, seventh, eighth, or any number of series of CT images of the core sample 108 with each series having a respective load profile. In some embodiments, the method 300 may include obtaining (e.g., capturing) CT images of the core sample 108 at varying wavelengths (e.g., energies). For instance, the method 300 may include obtaining a CT image or series of CT images at a first wavelength and obtaining a CT image or series of CT images at a second, different wavelength. For example, images obtained via the method 300 may exhibit dual energies. In one or more embodiments, obtaining CT images art differing wavelengths (e.g., energies) may enable determining different properties of the core sample 108 (e.g., a chemical property and a mineral property of the core sample 108).

Rotating the core sample 108 may include rotating the entire core holder assembly 102 relative to the imager system 104. In some embodiments, the core holder assembly 102 may be coupled to a vice and/or a rotatable base, and the core holder assembly 102 may be rotated by the vice and/or the rotatable base via a motor. In some embodiments, rotating the core sample 108 may include stopping rotation at each rotation point where a CT image is captured. In other embodiments, the rotation may be continuous.

In some embodiments, obtaining the series of CT images of the core sample may include at least partially saturating the core sample 108 with a doped fluid. For example, the core sample 108 may be saturated with a fluid having a predetermine X-ray attenuation coefficient (e.g., an X-ray attenuating solute). In some embodiments, the dopant of the fluid may include materials having relatively high-electron densities and/or high effective atomic number elements. As will be discussed in greater detail below, utilizing a doped fluid to saturate the core sample 108 may provide data (e.g., rock mechanical properties) as a function of fluid type and/or displacement to be measured in one or more of a micrometer-determined projection or a cubic micrometer-determined three-dimensional mode.

Furthermore, the method 300 may include generating a three-dimensional representation of at least a portion of the core sample 108 based on the obtained series of computed tomography images of the core sample 108, as shown in act 350 of FIG. 3. In some embodiments, generating a three-dimensional representation (e.g., a volumetric map of X-ray attenuation) of at least a portion of the core sample 108 may include reconstructing at least a portion of the volume of the core sample 108 based on the obtained series of computed tomography images. For instance, the method 300 may include generating at least a portion of the core sample 108 in three-dimensional space utilizing a Radon transform (i.e., an integral transform whose inverse is used to reconstruct images from CT scans). For example, the method 300 may include generating at least a portion of the core sample 108 in three-dimensional space utilizing one or more of the following equations:

The Radon transform can be defined by:

$$R(p, \tau)[f(x, y)] = \int_{-\infty}^{\infty} f(x, \tau + px)dx \qquad (1)$$

$$= \int_{-\infty}^{\infty}\int_{-\infty}^{\infty} f(x, y)\delta[y - (\tau + px)]dydx \qquad (2)$$

$$\equiv U(p, \tau), \qquad (3)$$

where P is the slope of a line, $\tau$ is its intercept, and $\delta(x)$ is the delta function. The inverse Radon transform is $$f(x, y) = \frac{1}{2\pi} \int_{-\infty}^{\infty} \frac{d}{dy} H[U(p, y - px)]dp, \qquad (4)$$

where H is a Hilbert transform. The transform can also be defined by:

$$R'(r,\alpha)[f(x,y)] = \int_{-\infty}^{\infty}\int_{-\infty}^{\infty} f(x,y)\delta(r - x\cos\alpha - y\sin\alpha)dxdy \qquad (5)$$

where r is the perpendicular distance from a line to the origin and $\alpha$ is the angle formed by the distance vector.

Using the identity:

$$\mathcal{F}_{\omega,\alpha}[R[f(\omega,\alpha)]](x,y) = \mathcal{F}^2_{u,v}[f(u,v)](x,y), \qquad (6)$$

where $\mathcal{F}$ is the Fourier transform, gives the inversion formula $$f(x, y) = c\int_0^\pi \int_{-\infty}^{\infty} \mathcal{F}_{\omega\alpha}[R[f(\omega, \alpha)]]|\omega|e^{i\omega(\alpha\cos\alpha + y\sin\alpha)}d\omega d\alpha. \qquad (7)$$

The Fourier transform can be eliminated according to the following:

$$f(x,y) = \int_0^\pi \int_{-\infty}^{\infty} R[f(r,\alpha)]W(r,\alpha,x,y)drd\alpha, \qquad (8)$$

where W is a weighting function such as $$W(r,\alpha,x,y) = h(x\cos\alpha + y\sin\alpha - r) = \mathcal{F}^{-1}[|\omega|]. \qquad (9)$$

Furthermore, utilizing the Radon transform, the method 300 may include combining multiple correlating pixels of the images of the series of CT images to generate a cubic voxel representing each set of correlating pixels (e.g., a set of pixels including a same pixel from each image of the series of CT images).

The method 300 may further include measuring a displacement of at least one characteristic of the core sample 108 due to the applied one or more loads and/or pore fluid pressures, as shown in act 360 of FIG. 3. The at least one characteristic may include pore boundaries, pore volumes, grain boundaries, grain volumes, electron densities, photoelectric effects, fractures or cracks, outer surfaces of the core sample 108. In some embodiments, the displacement may be measured relative to the core sample 108 not being subjected to any load profile. Additionally, in one or more embodiments, the displacement may be measured relative to the core sample being subjected to another load profile. For example, when the displacement of a characteristic is measured based on a two-dimensional image, the displacement may be measured in axes (e.g., planes) orthogonal to the axis (e.g., plane) upon which the image is captured. Moreover, based on the generated three-dimensional representation, the displacement may be measured in three dimensions. For instance, in some embodiments, the displacements of the at least one characteristic depicted in each image of the series of images may be combined via any of the manners described above to determine a three-dimensional displacement (e.g., distances in each dimension). Furthermore, in one or more embodiments, the displacements may be determined as a function of the applied load profile (e.g., stresses). In some embodiments, the displacements for a given characteristic may be measured automatically via the controller 105. In other embodiments, the displacements for a given characteristic may be measured manually or in combination with automatic functions. In view of the foregoing, the method 300 described herein enables displacement to be measured in either micrometer-determined projection or cubic micrometer-determined three-dimensional modes.

Figure 4:
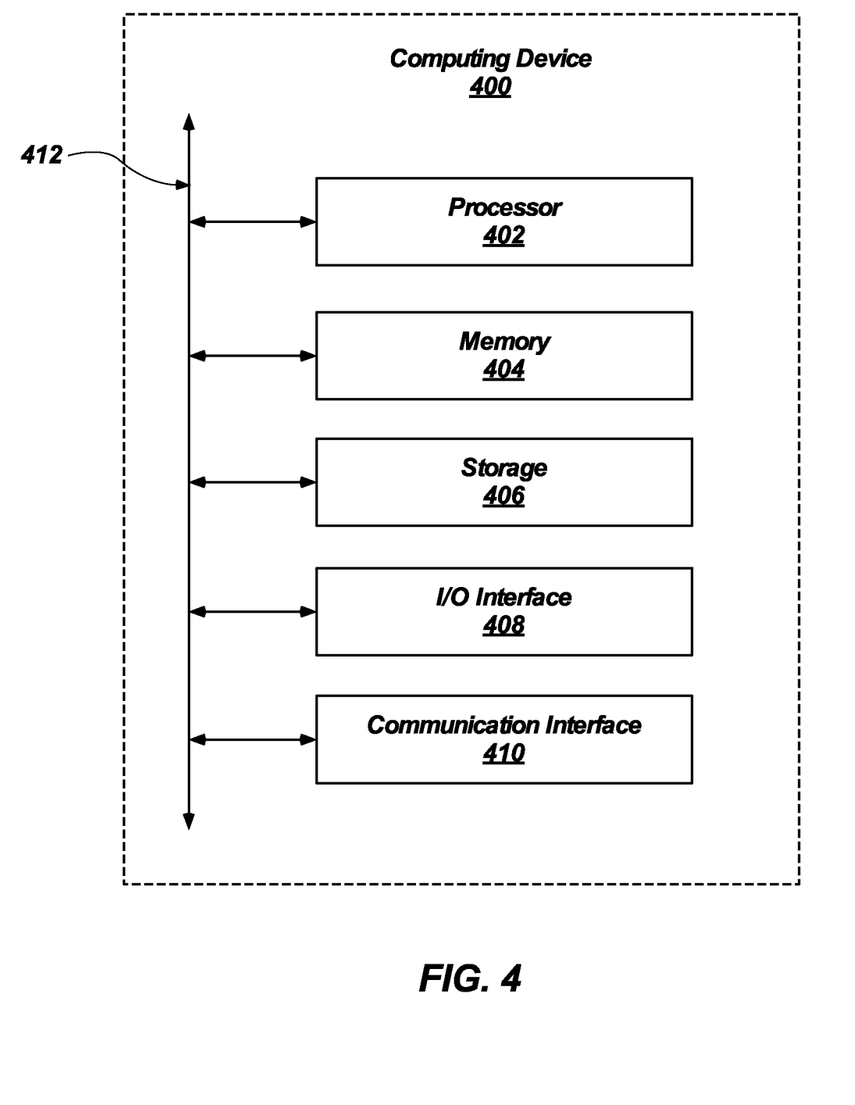
FIG. 4 is schematic diagram of a core-analysis control system according to one or more embodiments of the present disclosure.

Additionally, the method 300 may include determining, based at least partially on the measured displacement of the at least one characteristic of the core sample 108, at least one property of the formation and/or the core sample 108, as shown in act 370 of FIG. 4. In some embodiments, the at least one property may include rock mechanical properties. For instance, the at least one property may include confined compressive strength, unconfined compressive strength, Poisson's ratio in multiple directions, a porosity (e.g., a derived porosity), a permeability (e.g., a simulated permeability), a bulk density, a grain density, a bulk-grain density porosity, a chemical and/or mineral property including minerology grain/clast size, a flexural moduli, a composition, an effective failure stress. The foregoing properties may be determined via known manners based on the measured displacement or x-ray attenuation of the at least one characteristic of the core sample 108. Furthermore, the foregoing properties may be determined based on measurements on the grain scale (e.g., micrometer scale) and/or the core sample scale (e.g., millimeter scale). Additionally, relationships between the properties and the grain scale and core sample scale may be determined.

In some embodiments, changes in properties from the micrometer grain scale to the millimeter core sample scale may be determined, and the relationship of the properties and changes in properties of each formation rock type may be parameterized. Moreover, in one or more embodiments, the properties may be determined at functions of the scale within which the properties are measured and as a function of the applied load profile (e.g., as a function of the applied stress). Furthermore, changes in the properties may be determined as a function of the applied load profiles (e.g., changes in load profiles).

As noted above, in some embodiments, the core sample 108 may be at least partially saturated with a doped fluid, and in such embodiments, the properties and or changes in properties may be determined as a function of the fluid type.

Referring to FIGS. 1A-3 together, the core analysis system 100 of the present disclosure is advantageous over conventional methods of determining and estimating rock mechanical properties. For example, conventional downhole sonic logs and load frame measurements typically cannot determine microscale rock mechanical and/or compositional properties, which control/effect far-field (wellbore distal) fracture propagation in reservoirs, at the grain scale. The foregoing often leads to errors in fracture models and operator completion designs. Conversely, as discussed above, the core analysis system 100 and methods of the present disclosure can determine microscale rock mechanical and/or compositional properties, which will improve accuracy of fracture models and operator completion designs. Furthermore, conventional downhole sonic logs and load frame measurements typically cannot provide/determine changes in the rock mechanical properties as a function of or with mineralogy parameters at the grain scale or sample-size scale. On the other hand, as discussed above, the core analysis system 100 and methods of the present disclosure can determine changes in rock mechanical properties as a function of or in conjunction with mineralogy parameters, or the rock mechanical properties can be correlated with mineralogy parameters of the formation. Accordingly, the core analysis system 100 and methods of the present disclosure may provide more accurate inputs for brittleness and fraccability logs.

Moreover, sonic logs are typically relatively expensive and are subject to calibration and interpretation error. Likewise, load frame measurements are typically relatively expensive, time-intensive, and subject to other experimental challenges such as health, safety, and environmental limitations, as well as high temperature limitations. Conversely, the core analysis system 100 and methods of the present disclosure are not limited by the calibration and interpretation error of sonic logs and are not subject to downhole conditions. Additionally, in comparison to conventional methods, the core analysis system 100 and methods of the present disclosure provide a low cost and faster turnaround time solution. Moreover, the results provided by the core analysis system 100 and methods of the present disclosure are client-ready and can be combined with dual-energy CT derived, micrometer-determined 3D mineralogy to provide more accurate facture models and/or logs.

FIG. 4 is a block diagram of a controller 105 according to one or more embodiments of the present disclosure. As shown in FIG. 4, in some embodiments, the controller 105 may include a core-analysis control system 400 (e.g., computing device). One will appreciate that one or more computing devices may implement the core-analysis control system 400. The core-analysis control system 400 can comprise a processor 402, a memory 404, a storage device 406, an I/O interface 408, and a communication interface 410, which may be communicatively coupled by way of a communication infrastructure 412. While an exemplary computing device is shown in FIG. 4, the components illustrated in FIG. 4 are not intended to be limiting. Additional or alternative components may be used in other embodiments. Furthermore, in certain embodiments, the core-analysis control system 400 can include fewer components than those shown in FIG. 4. Components of the core-analysis control system 400 shown in FIG. 4 will now be described in additional detail.

In one or more embodiments, the processor 402 includes hardware for executing instructions, such as those making up a computer program. As an example and not by way of limitation, to execute instructions, the processor 402 may retrieve (or fetch) the instructions from an internal register, an internal cache, the memory 404, or the storage device 406 and decode and execute them. In one or more embodiments, the processor 402 may include one or more internal caches for data, instructions, or addresses. As an example and not by way of limitation, the processor 402 may include one or more instruction caches, one or more data caches, and one or more translation lookaside buffers (TLBs). Instructions in the instruction caches may be copies of instructions in the memory 404 or the storage 406.

The memory 404 may be used for storing data, metadata, and programs for execution by the processor(s). The memory 404 may include one or more of volatile and non-volatile memories, such as Random Access Memory ("RAM"), Read-Only Memory ("ROM"), a solid state disk ("SSD"), Flash memory, Phase Change Memory ("PCM"), or other types of data storage. The memory 404 may be internal or distributed memory.

The storage device 406 includes storage for storing data or instructions. As an example and not by way of limitation, storage device 406 can comprise a non-transitory storage medium described above. The storage device 406 may include a hard disk drive (HDD), a floppy disk drive, flash memory, an optical disc, a magneto-optical disc, magnetic tape, or a Universal Serial Bus (USB) drive or a combination of two or more of these. The storage device 406 may include removable or non-removable (or fixed) media, where appropriate. The storage device 406 may be internal or external to the core-analysis control system 400. In one or more embodiments, the storage device 406 is non-volatile, solid-state memory. In other embodiments, the storage device 406 includes read-only memory (ROM). Where appropriate, this ROM may be mask programmed ROM, programmable ROM (PROM), erasable PROM (EPROM), electrically erasable PROM (EEPROM), electrically alterable ROM (EAROM), or flash memory or a combination of two or more of these.

The I/O interface 408 allows a user to provide input to, receive output from, and otherwise transfer data to and receive data from core-analysis control system 400. The I/O interface 408 may include a mouse, a keypad or a keyboard, a touch screen, a camera, an optical scanner, network interface, modem, other known I/O devices or a combination of such I/O interfaces. The I/O interface 408 may include one or more devices for presenting output to a user, including, but not limited to, a graphics engine, a display (e.g., a display screen), one or more output drivers (e.g., display drivers), one or more audio speakers, and one or more audio drivers. In certain embodiments, the I/O interface 408 is configured to provide graphical data to a display for presentation to a user. The graphical data may be representative of one or more graphical user interfaces and/or any other graphical content as may serve a particular implementation.

The communication interface 410 can include hardware, software, or both. In any event, the communication interface 410 can provide one or more interfaces for communication (such as, for example, packet-based communication) between the core-analysis control system 400 and one or more other computing devices or networks. As an example and not by way of limitation, the communication interface 410 may include a network interface controller (NIC) or network adapter for communicating with an Ethernet or other wire-based network or a wireless NIC (WNIC) or wireless adapter for communicating with a wireless network, such as a WI-FI.

Additionally or alternatively, the communication interface 410 may facilitate communications with an ad hoc network, a personal area network (PAN), a local area network (LAN), a wide area network (WAN), a metropolitan area network (MAN), or one or more portions of the Internet or a combination of two or more of these. One or more portions of one or more of these networks may be wired or wireless. As an example, the communication interface 410 may facilitate communications with a wireless PAN (WPAN) (such as, for example, a BLUETOOTH® WPAN), a WI-FI network, a WI-MAX network, a cellular telephone network (such as, for example, a Global System for Mobile Communications (GSM) network), or other suitable wireless network or a combination thereof.

Additionally, the communication interface 410 may facilitate communications various communication protocols. Examples of communication protocols that may be used include, but are not limited to, data transmission media, communications devices, Transmission Control Protocol ("TCP"), Internet Protocol ("IP"), File Transfer Protocol ("FTP"), Telnet, Hypertext Transfer Protocol ("HTTP"), Hypertext Transfer Protocol Secure ("HTTPS"), Session Initiation Protocol ("SIP"), Simple Object Access Protocol ("SOAP"), Extensible Mark-up Language ("XML") and variations thereof, Simple Mail Transfer Protocol ("SMTP"), Real-Time Transport Protocol ("RTP"), User Datagram Protocol ("UDP"), Global System for Mobile Communications ("GSM") technologies, Code Division Multiple Access ("CDMA") technologies, Time Division Multiple Access ("TDMA") technologies, Short Message Service ("SMS"), Multimedia Message Service ("MMS"), radio frequency ("RF") signaling technologies, Long Term Evolution ("LTE") technologies, wireless communication technologies, in-band and out-of-band signaling technologies, and other suitable communications networks and technologies.

The communication infrastructure 412 may include hardware, software, or both that couples components of the core-analysis control system 400 to each other. As an example and not by way of limitation, the communication infrastructure 412 may include an Accelerated Graphics Port (AGP) or other graphics bus, an Enhanced Industry Standard Architecture (EISA) bus, a front-side bus (FSB), a HYPER-TRANSPORT (HT) interconnect, an Industry Standard Architecture (ISA) bus, an INFINIBAND interconnect, a low-pin-count (LPC) bus, a memory bus, a Micro Channel Architecture (MCA) bus, a Peripheral Component Interconnect (PCI) bus, a PCI-Express (PCIe) bus, a serial advanced technology attachment (SATA) bus, a Video Electronics Standards Association local (VLB) bus, or another suitable bus or a combination thereof.

The present disclosure also include the following embodiments:

Embodiment 1. A method of determining properties of a core sample, the method comprising: disposing a core sample of a formation within a core holder assembly; applying one or more pressures to the core sample; obtaining at least one computed tomography image of the core sample; and based on the at least one computed tomography image of the core sample, determining at least one property of the core sample as a function of the applied one or more pressures.

Embodiment 2. The method of embodiment 1, wherein applying one or more pressures to the core sample comprises applying at least one of an axial pressure, a radial pressure, or a pore fluid pressure to the core sample.

Embodiment 3. The method of any one of embodiments 1 and 2, wherein obtaining at least one computed tomography image of the core sample comprises: rotating the core sample about a longitudinal axis of the core holder assembly; and obtaining a series of computed tomography images of the core sample, wherein the series of computed tomography images includes an image for at least every degree of rotation of the core sample.

Embodiment 4. The method of embodiment 3, wherein the series of computed tomography images includes an image for at least every half degree of rotation of the core sample.

Embodiment 5. The method of any one of embodiments 3 and 4, wherein determining at least one property of the core sample comprises utilizing a radon transform to transform two-dimensional pixels into cubic voxels.

Embodiment 6. The method of embodiment 5, wherein determining at least one property of the core sample further comprises measuring a displacement of at least one characteristic of the core sample in three dimensions.

Embodiment 7. The method of embodiment 6, wherein determining at least one property of the core sample further comprises deriving porosity of at least a portion of the core sample based on measured displacements of the at least one characteristic.

Embodiment 8. The method of any one of embodiments 6 and 7, wherein determining at least one property of the core sample further comprises simulating a permeability of the core sample based on the measured displacement of the at least one characteristic of the core sample.

Embodiment 9. The method of any one of embodiments 6-8, wherein determining at least one property of the core sample further comprises determining a confined compressive strength of the core sample based at least partially on the measured displacement of the at least one characteristic of the core sample.

Embodiment 10. The method of any one of embodiments 1-9, wherein determining at least one property of the core sample further comprises measuring a dilation of at least one pore of the core sample in at least one dimension.

Embodiment 11. The method of any one of embodiments 1-10, further comprising at least partially saturating the core sample with a fluid comprising brine and oil.

Embodiment 12. The method of any one of embodiments 1-11, further comprising at least partially saturating the core sample with a doped fluid.

Embodiment 13. A core analysis system for determining properties of a core sample, comprising: a core holder assembly; a computed tomography imager; and a core-analysis control system operably coupled to the core holder assembly and the computed tomography imager, the core-analysis control system comprising: at least one processor; and at least one non-transitory computer-readable storage medium storing instructions thereon that, when executed by the at least one processor, cause the core analysis system to: apply, via the core holder assembly, one or more pressures to a core sample of a formation disposed within the core holder assembly; rotate the core holder assembly about a center longitudinal axis of the core holder assembly; obtain, via the computed tomography imager, a series of computed tomography images of the core sample at different rotation increments of the core holder assembly; generate, based on the series of computed tomography images of the core sample, a three-dimensional representation of at least a portion the core sample utilizing a radon transform; and measure a displacement of at least one characteristic of the core sample due to the applied one or more pressures.

Embodiment 14. The core analysis system of embodiment 13, wherein applying one or more pressures to the core sample comprises applying at least one of an axial pressure, a radial pressure, or a pore fluid pressure to the core sample.

Embodiment 15. The core analysis system of embodiment 13, wherein generating a three-dimensional representation of the core sample utilizing a radon transform comprises generating a cubic voxel for each set of correlating two-dimensional pixels within the series of computed tomography images of the core sample.

Embodiment 16. The core analysis system of embodiment 13, further comprising instructions that, when executed by the at least one processor, cause the core analysis system to determine at least one property of the core sample based at least partially the measured displacement of at least one characteristic of the core sample.

Embodiment 17. The core analysis system of embodiment 16, wherein the at least one property of the core sample comprises one or more of confined compressive strength, an unconfined compressive strength, simulated permeability, derived porosity, chemical properties, mineralogy properties, grain/clast sizes, flexural moduli, or a composition of the core sample.

Embodiment 18. The core analysis system of embodiment 13, further comprising instructions that, when executed by the at least one processor, cause the core analysis system to at least partially saturate the core sample with a fluid comprising brine and oil.

Embodiment 19. The core analysis system of embodiment 13, further comprising instructions that, when executed by the at least one processor, cause the core analysis system to at least partially saturate the core sample with a doped fluid.

Embodiment 20. A method of determining properties of a core sample, the method comprising: disposing a core sample of a formation within a core holder assembly; applying one or more pressures to the core sample; rotating the core sample about a center longitudinal axis of the core holder assembly; obtaining a series of computed tomography images of the core sample at different rotation increments of the core sample; generating, based at least partially on the obtained series of computed tomography images of the core sample, a three-dimensional representation of at least a portion of the core sample utilizing a radon transform; measuring a displacement of at least one characteristic of the core sample due to the applied one or more pressures; and based at least partially on the measured displacement, determining at least one property of the core sample as a function of the applied one or more pressures.

The embodiments of the disclosure described above and illustrated in the accompanying drawings do not limit the scope of the disclosure, which is encompassed by the scope of the appended claims and their legal equivalents. Any equivalent embodiments are within the scope of this disclosure. Indeed, various modifications of the disclosure, in addition to those shown and described herein, such as alternative useful combinations of the elements described, will become apparent to those skilled in the art from the description. Such modifications and embodiments also fall within the scope of the appended claims and equivalents.

What is claimed is:

1. A method of determining properties of a core sample, the method comprising:
   disposing a core sample of a formation within a pressure chamber of a core holder assembly;
   applying one or more pressures to the core sample within the pressure chamber;
   obtaining at least one computed tomography image of the core sample; and
   based on the at least one computed tomography image of the core sample, determining at least one property of the core sample as a function of the applied one or more pressures.

2. The method of claim 1, wherein applying one or more of pressures to the core sample comprises applying at least one of an axial pressure, a radial pressure, or a pore fluid pressure to the core sample.

3. The method of claim 1, wherein obtaining at least one computed tomography image of the core sample comprises:
   rotating the core sample about a longitudinal axis of the core holder assembly; and
   obtaining a series of computed tomography images of the core sample, wherein the series of computed tomography images includes an image for at least every degree of rotation of the core sample.

4. The method of claim 3, wherein the series of computed tomography images includes an image for at least every half degree of rotation of the core sample.

5. The method of claim 3, wherein determining at least one property of the core sample comprises utilizing a radon transform to transform two-dimensional pixels into cubic voxels.

6. The method of claim 5, wherein determining at least one property of the core sample further comprises measuring a displacement of at least one characteristic of the core sample in three dimensions.

7. The method of claim 6, wherein determining at least one property of the core sample further comprises deriving porosity of at least a portion of the core sample based on the measured displacement of the at least one characteristic of the core sample.

8. The method of claim 6, wherein determining at least one property of the core sample further comprises simulating a permeability of the core sample based on the measured displacement of the at least one characteristic of the core sample.

9. The method of claim 6, wherein determining at least one property of the core sample further comprises determining a confined compressive strength of the core sample based at least partially on the measured displacement of the at least one characteristic of the core sample.

10. The method of claim 1, wherein determining at least one property of the core sample further comprises measuring a dilation of at least one pore of the core sample in at least one dimension.

11. The method of claim 1, further comprising at least partially saturating the core sample with a fluid comprising brine or oil.

12. The method of claim 1, further comprising at least partially saturating the core sample with a doped fluid.

13. A core analysis system for determining properties of a core sample, comprising:
   a core holder assembly;
   a computed tomography imager; and
   a core-analysis control system operably coupled to the core holder assembly and the computed tomography imager, the core-analysis control system comprising:
      at least one processor; and
      at least one non-transitory computer-readable storage medium storing instructions thereon that, when executed by the at least one processor, cause the core analysis system to:
         apply, via the core holder assembly, one or more pressures to a core sample of a formation disposed within the core holder assembly;

rotate the core holder assembly about a center longitudinal axis of the core holder assembly;

obtain, via the computed tomography imager, a series of computed tomography images of the core sample at different rotation increments of the core holder assembly;

generate, based on the series of computed tomography images of the core sample, a three-dimensional representation of at least a portion the core sample utilizing a radon transform; and measure a displacement of at least one characteristic of the core sample due to the applied pressures.

14. The core analysis system of claim 13, wherein applying one or more of pressures to the core sample comprises applying at least one of an axial pressure, a radial pressure, or a pore fluid pressure to the core sample.

15. The core analysis system of claim 13, wherein generating a three-dimensional representation of the core sample utilizing a radon transform comprises generating a cubic voxel for a set of correlating two-dimensional pixels within the series of computed tomography images of the core sample.

16. The core analysis system of claim 13, further comprising instructions that, when executed by the at least one processor, cause the core analysis system to determine at least one property of the core sample based at least partially the on measured displacement of at least one characteristic of the core sample.

17. The core analysis system of claim 16, wherein the at least one property of the core sample comprises one or more of a confined compressive strength, an unconfined compressive strength, a simulated permeability, a derived porosity, chemical properties, mineralogy properties, grain/clast sizes, flexural moduli, or a composition of the core sample.

18. The core analysis system of claim 13, further comprising instructions that, when executed by the at least one processor, cause the core analysis system to at least partially saturate the core sample with a fluid comprising brine or oil.

19. The core analysis system of claim 13, further comprising instructions that, when executed by the at least one processor, cause the core analysis system to at least partially saturate the core sample with a doped fluid.

20. A method of determining properties of a core sample, the method comprising:

disposing a core sample of a formation within a core holder assembly;

applying one or more pressures to the core sample;

rotating the core sample about a center longitudinal axis of the core holder assembly;

obtaining a series of computed tomography images of the core sample at different rotation increments of the core sample;

generating, based at least partially on the obtained series of computed tomography images of the core sample, a three-dimensional representation of at least a portion of the core sample utilizing a radon transform;

measuring a displacement of at least one characteristic of the core sample due to the applied one or more pressures; and based at least partially on the measured displacement, determining at least one property of the core sample as a function of at least one of the applied one or more pressures or energies of applied x-rays.

* * * * *